US008246981B2

(12) United States Patent
Patel et al.

(10) Patent No.: US 8,246,981 B2
(45) Date of Patent: Aug. 21, 2012

(54) TRANSDERMAL METHOD AND PATCH FOR EMESIS

(75) Inventors: Kalpana J Patel, West Windsor, NJ (US); Suresh Borsadia, Plainsboro, NJ (US)

(73) Assignee: Abeille Pharamaceuticals, Inc., Princeton, NJ (US)

( * ) Notice: Subject to any disclaimer, the term of this patent is extended or adjusted under 35 U.S.C. 154(b) by 839 days.

(21) Appl. No.: 11/558,663

(22) Filed: Nov. 10, 2006

(65) Prior Publication Data

US 2007/0087044 A1 Apr. 19, 2007

Related U.S. Application Data

(63) Continuation-in-part of application No. 11/380,268, filed on Apr. 26, 2006, now abandoned.

(60) Provisional application No. 60/682,251, filed on May 18, 2005, provisional application No. 60/702,744, filed on Jul. 27, 2005, provisional application No. 60/759,381, filed on Jan. 17, 2006.

(51) Int. Cl.
*A61K 9/70* (2006.01)
(52) U.S. Cl. ...................................... 424/449
(58) Field of Classification Search ............. 424/449
See application file for complete search history.

(56) References Cited

U.S. PATENT DOCUMENTS

| 3,269,994 | A | 8/1966 | Horn et al. |
|---|---|---|---|
| 5,166,145 | A | 11/1992 | Jao et al. |
| 5,310,561 | A | 5/1994 | Jao et al. |
| 5,482,716 | A | 1/1996 | Tyers et al. |
| 5,656,286 | A | 8/1997 | Miranda et al. |
| 5,929,059 | A | 7/1999 | Sanger et al. |
| 5,951,999 | A | 9/1999 | Therriault et al. |
| 6,136,807 | A | 10/2000 | Braun |
| 6,174,546 | B1 | 1/2001 | Therriault et al. |
| 6,239,228 | B1 | 5/2001 | Zajaczkowski et al. |
| 6,440,453 | B1 | 8/2002 | Fischer et al. |
| 6,495,159 | B2 | 12/2002 | Hirano et al. |
| 6,512,010 | B1 * | 1/2003 | Gale et al. ............. 514/649 |
| 6,544,550 | B1 | 4/2003 | Tyers et al. |
| 6,719,997 | B2 | 4/2004 | Hsu et al. |
| 2003/0175354 | A1 | 9/2003 | Drizen et al. |
| 2004/0013621 | A1 | 1/2004 | Klose et al. |
| 2006/0177493 | A1 | 8/2006 | Altenschopfer |

FOREIGN PATENT DOCUMENTS

| CA | 2341998-0 | 9/2002 |
|---|---|---|
| EP | 1 064 939 | 6/2000 |
| EP | 1 044 684 A2 | 10/2000 |
| EP | 1 163 902-0 | 12/2001 |
| JP | 08-034731 | 2/1996 |
| WO | WO-94/01095-0 | 1/1994 |
| WO | WO-94/07468-0 | 4/1994 |
| WO | WO/9837111 | 8/1998 |
| WO | WO/9853815 | 12/1998 |
| WO | 0047208 A1 | 8/2000 |
| WO | WO 00/47208 | 8/2000 |
| WO | WO-01/74338 | 10/2001 |
| WO | WO 2004/000263 A1 | 12/2003 |
| WO | WO 2004/000275 A1 | 12/2003 |
| WO | WO 2004/000358 A1 | 12/2003 |
| WO | WO 2004/039427 A2 | 5/2004 |
| WO | WO 2004/069141 A2 | 8/2004 |
| WO | WO 03/013482 | 11/2005 |
| WO | WO 2006/028863 A1 | 3/2006 |

OTHER PUBLICATIONS

Schulte, Marvin K., et al. "Functional group interactions of a 5-HT3R antagonist", BMC Biochemistry, 3:16, 2002. Published Jun. 13, 2002.*
Biswas and Rudra, Comparison of granisetron and granisetron plus dexamethasone for the prevention of postoperative nausea and vomiting after laparoscopic cholecystectomy. Acta Anaesthesiol Scand., 47:79-83, 2003.
Cupissol et al., Evaluation of the bioequivalence of tablet and capsule formulations of granisetron in patients undergoing cytotoxic chemotherapy for a malignant disease. J.Pharm.Sci., 82:1281-1284, 1993.
Friedman et al., Oral granisetron for the prevention of acute late onset nausea and vomiting in patients treated with moderately emetogenic chemotherapy. Oncologist, 5:136-143, 2000.
Gralla et al., Recommendations for the use of antiemetics: Evidence based, clinical practice guidelines. Journal of Clinical Oncology, 17:2971-2994, 1999.
Guillem et al., High efficacy of oral granisetron in the total control of cyclophosphamide-induced prolonged emesis. Proceedings of the American Society of Oncology, 17:46, 1998.
Kalaycio et al., Continuous-infusion granisetron compared to ondansetron for the prevention of nausea and vomiting after high-dose chemotherapy. J. Cancer Res. Clin. Oncol., 124:265-269, 1998.
Noble et al., A double-blind, randomized, crossover comparison of granisetron and ondansetron in 5-day fractionated chemotherapy: assessment of efficacy, safety and patient preference. Eur. J. of Cancer, 30: 1083-1088, 1994.
Physicians Desk Reference (2001) entry for Kytril®.
Porzio et al., Pruritus in a patient with advanced cancer successfully treated with continuous infusion of granisetron. Support Care Cancer, Jan. 21, 2004.
Rolla, et al., New Antiemetic Drugs, Annals of Oncology 17 (Supplement 2) ii96-ii100, 2006 doi:10 1093/annoc/md,936.

* cited by examiner

*Primary Examiner* — Richard Schnizer
*Assistant Examiner* — Audrea Buckley
(74) *Attorney, Agent, or Firm* — Moser Taboada

(57) ABSTRACT

Provided, among other things, is a method of treating acute, delayed or anticipatory emesis for a sustained period in an individual, which involves applying to a portion of intact skin on the individual a composition of
  i. an antiemetically effective amount of a 5-$HT_3$ receptor antagonist;
  ii. a permeation enhancing amount of permeation enhancer comprising 0.5% to 15% by weight of the skin-contacting layer; and
  iii. an adhesive.

27 Claims, 2 Drawing Sheets

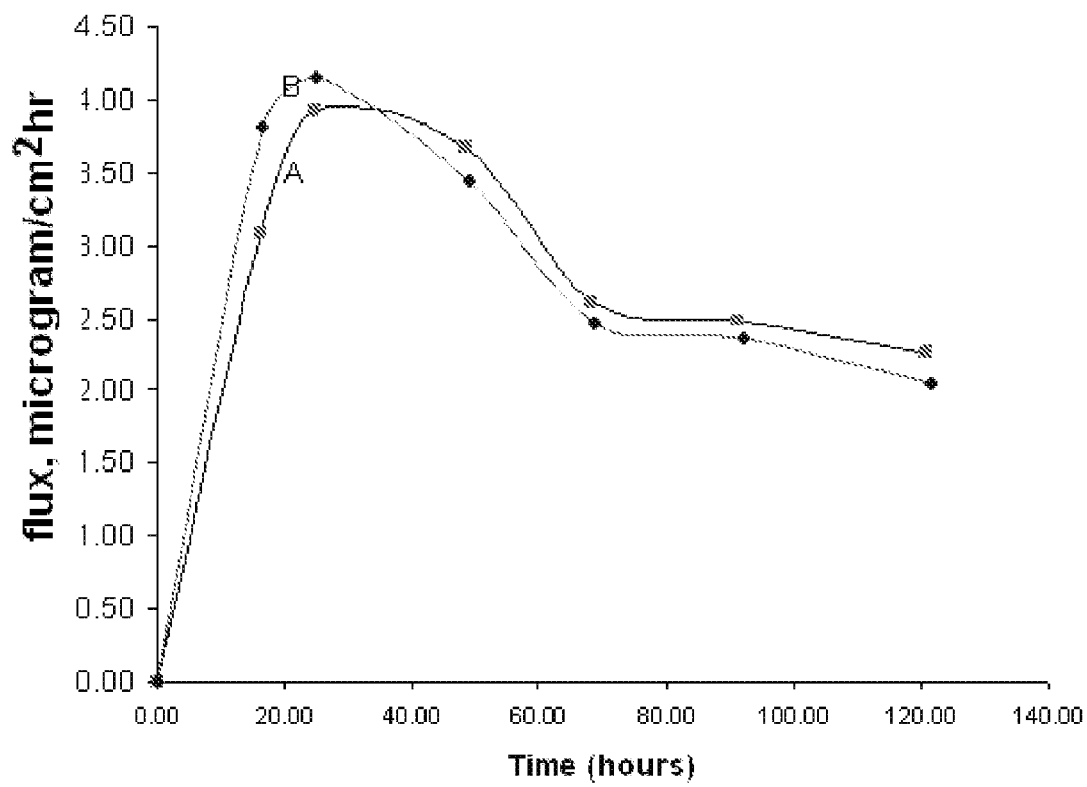
Figure 1. Granisetron Rate of Flux
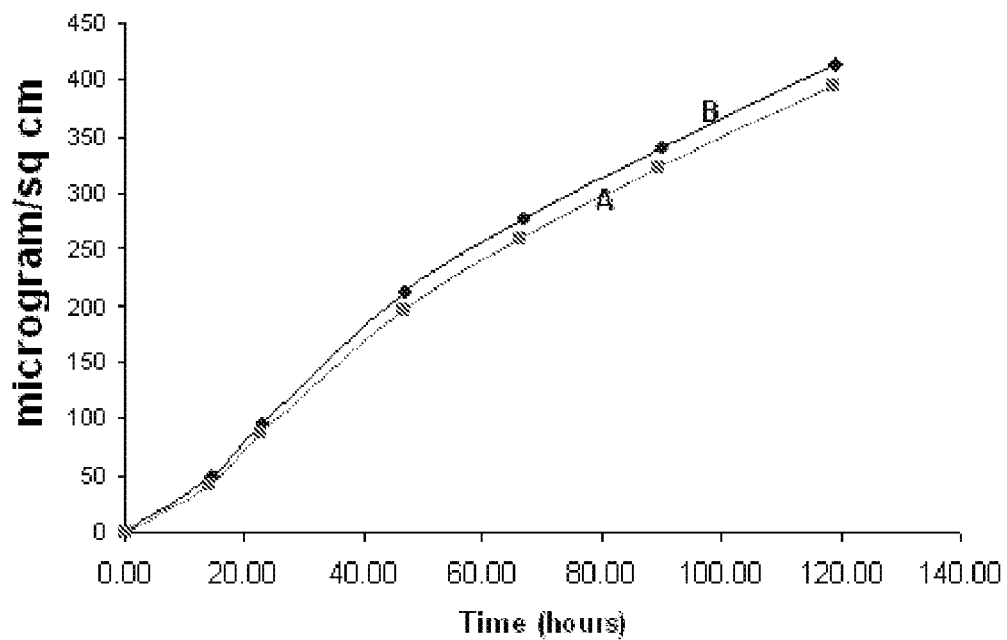
Figure 2. Cumulative Amount of Granisetron

TRANSDERMAL METHOD AND PATCH FOR EMESIS

This application is a Continuation-in-Part of U.S. application Ser. No. 11/380,268, filed Apr. 26, 2006 now abandoned, which claims the priority of U.S. Application 60/682,251, filed May 18, 2005, U.S. Application 60/702,744, filed Jul. 27, 2005, and U.S. Application 60/759,381, filed Jan. 17, 2006.

The present invention relates to a transdermal device and method for the treatment of nausea and vomiting, and more particularly to a transdermal method, composition, and device containing a 5-HT$_3$ receptor antagonist for the treatment of nausea and vomiting for a sustained period of time.

Most patients undergoing anticancer treatment either by chemotherapy or radiation suffer from side effects of the treatment such as nausea and vomiting, a common complaint by patients. To prevent or minimize these side effects of anticancer treatments, antagonists of 5-hydroxytryptamine subtype 3 (hereinafter referred to as 'serotonin') such as ondansetron, granisetron, tropisetron, dolasetron, hydrodolasetron, azasetron, ramosetron, lerisetron, indisetron, itasetron, palonosetron, lamosetron, allosetron and mixtures thereof, known as serotonin receptor antagonists or 5-HT$_3$ receptor antagonists, have been widely administered, either parenterally or orally, on multiple days.

Nausea and vomiting may also occur due to other reasons, such as for example, post-operatively, from motion sickness, or as a side effect of other drugs taken by a patient. Examples of drugs which may cause nausea and vomiting as side effects are certain antibacterial and antiviral agents, glucose-level-controlling bioactive agents, such as insulin and amylin or their natural and synthetic analogs, α-glucodase inhibitors, sulfonylurea, meglitinide, thiazolidinediones, biguanide, dual PPARα/γ agonists, PPARγ agonists, and insulin secretagogues.

Nausea or vomiting of unknown etiology, including cyclic vomiting syndrome, can also be debilitating to individuals. In cyclic vomiting syndrome (CVS), people experience bouts or cycles of severe nausea and vomiting that last for hours or even days and alternate with often longer periods of no symptoms. Each episode is similar to the previous ones. The episodes tend to start at about the same time of day, last the same length of time, and present the same symptoms at the same level of intensity. The pre-episodic symptoms can predict the forthcoming episode and define a "prodrome."

In any situation where a patient is suffering from nausea and vomiting, oral administration of an antiemetic agent is challenging and creates more discomfort for the patient. Intravenous (IV) or intramuscular (IM) administration is generally impractical for home use. Oral, IM, and IV dosages must be given to the patient in multiple doses over time to achieve continuous antiemetic benefits, although these administration routes provide fluctuating plasma levels of the antiemetic agent. Additionally, since nausea and vomiting are challenging to reverse, antiemetic agents are most effective if given prophylactically. Such prophylaxis is critical when nausea and vomiting are anticipated in advance as in case of chemotherapy, radiation treatment, application of the a pharmaceutical that causes emesis or during the prodrome period of CVS.

To cope with these problems, there has been an attempt to formulate a composition of an antiemetic agent in the form of patches so that the antiemetic agent can be administered transdermally.

Attempts to develop a transdermally administered antiemetic agent have raised other problems. For example, some penetration enhancers used in transdermal compositions, (e.g., terpenes), induce skin irritation. Alcohols, which are often needed to solubilize the antiemetic agent for transdermal applications, are also irritating to the skin. Also, because of rapid depletion of the alcohol, sustained delivery over a period greater than a few hours is difficult to achieve. When a transdermal composition consisting of a solution with a low viscosity is used, the blood level of the drug may easily drop below the effective level thus lessening the desired pharmacological effect.

Other efforts to administer antiemetic agents transdermally have included complicated application devices or techniques such as supplemental energy to enhance the transdermal penetration of the drug. Current art describing transdermal antiemetic treatments often focuses on mimicking oral or IV agents to achieve therapeutic plasma levels. Typical delivery of such agents has been attempted with the salt form of the drug to maintain the stability of the active agent. However, salt forms of antiemetic agents have relatively low transdermal permeabilities, and it is difficult to achieve therapeutic plasma levels over a sustained period. Use of the free base form is typically not considered since it could be irritating or considered to be unstable in the dosage form.

Thus, it is desirable to provide a transdermal composition of an antiemetic agent which is simple to use, nonirritating to the skin and which may be left in place on the skin for 24 hours, two days, three days or more for continuously and effectively preventing, ameliorating or treating nausea and vomiting. Moreover, with modest but functionally significant concentrations of active and permeation enhancer, it is nonetheless possible using the current teachings to formulate a patch that delivers antiemetic agent over a very substantial time period, and even maintain delivery as measured at the blood level well after removal of the composition.

Extended delivery to the blood has been reported, but using transdermal delivery devices that lacked permeation enhancer. See, WO 2004/069141. With the present invention, remarkably sustained delivery is achieved with the presence of functionally significant concentrations of permeation enhancer. The lack of permeation enhancer is taught in the '141 application to limit instability and irritation. The lack of permeation enhancer limits the maximum plasma concentration and total delivery of the active moiety. On the other hand, inclusion of permeation enhancer leads to irritating compositions. Surprisingly, therapeutic plasma levels are achieved and maintained using the teachings of the current invention, but using modest but functionally significant concentrations of permeation enhancer such that the final product is non irritating as well as stable.

SUMMARY OF THE INVENTION

Provided in one embodiment is a method of treating acute, delayed or anticipatory emesis for a sustained period in an individual, the method comprising: applying to a portion of intact skin or mucosa on the individual for 24 hours or more a composition comprising:
i. an antiemetically effective amount of a 5-HT3 receptor antagonist;
ii. a permeation enhancing amount of permeation enhancer comprising 0.5% to 15% by weight of the skin-contacting layer; and
iii. an adhesive,
wherein a plasma concentration of the 5-HT3 receptor antagonist in a therapeutically effective range is provided for period of time from an onset time to 12 hours or more after the composition is removed. In certain embodiments, 12 or more hours after removing the composition, one applies a second said composition, wherein a plasma concentration of the 5-HT3 receptor antagonist in a therapeutically effective range is provided for period of time from an onset time to 12 hours or more after the second said composition is removed.

In certain embodiments, the 5-HT3 receptor antagonist is administered in conjunction with another antiemetic agent, or the same agent in a separate form of administration.

Additionally provided is a composition for transdermal administration of an antiemetic comprising: a skin-contacting composition comprising:
i. an antiemetically effective amount of a 5-HT3 receptor antagonist;
ii. a permeation enhancing amount of permeation enhancer comprising 0.5% to 15% by weight of the skin-contacting layer; and
iii. an adhesive, wherein, when applied to a portion of intact skin on an individual for 24 hours (or more) and then removed, the composition provides the individual with a plasma concentration of the 5-HT3 receptor antagonist in a therapeutically effective range for period of time from an onset time to 12 hours or more after the composition is removed.

Further provided is a device for transdermal prevention, amelioration or treatment of nausea and vomiting in an individual which comprises a patch comprising: (a) a support layer; and (b) a skin-contacting layer comprising:
i. an antiemetically effective amount of a 5-HT3 receptor antagonist;
ii. a permeation enhancing amount of permeation enhancer comprising 0.5% to 15% by weight of the skin-contacting layer; and
iii. an adhesive, wherein, when applied to a portion of intact skin on an individual for 24 hours (or more) and then removed, the device surprisingly provides the individual with a plasma concentration of the 5-HT3 receptor antagonist in a therapeutically effective range for period of time from an onset time to 12 hours or more after the device is removed.

In a preferred embodiment, the formulation surprisingly exhibits minimal irritation despite the presence of permeation enhancer and active ingredient. The irritation scores after the first application were less than 1.0.

Further provided is a device for transdermal application for the prevention, amelioration or treatment of nausea and vomiting which can be applied between 30 minutes to 36 hours prior to the expected or anticipated nausea and vomiting (such as 2-36 hours, 12 hours, 24 hours, and the like).

In a one embodiment, the composition exhibits one or more of the following in vivo average plasma profiles in adults:

i. The transdermal composition provides 1 ng/ml or more (such as 2 ng/ml or more) of plasma concentrations during all of 6 to 24 hours after patch application, or during all of 6 to 36 hours after patch application.

ii. The transdermal composition provides plasma levels that are significantly lower than achieved by a bolus parenteral administration (e.g., IV injection) of a standard therapeutic parenteral dose of the same HT3 receptor antagonist.

iii. iii. The transdermal composition (e.g., as formulated with 15 to 25 mg of 5-HT3 receptor antagonist in case of granisetron) provides 75% or more of the total exposure (as defined by area under the curve) achieved by total standard daily dose (for e.g. 2 mg/day in case of granisetron) of oral administration of the same HT3 receptor antagonist (either in single or divided doses) for 3 days during which the that the patch is worn, or for 4 days during which the that the patch is worn, or for 5 days during which the that the patch is worn.

iv. The transdermal (such as of granisetron) provides a plasma concentration of the 5-HT$_3$ receptor antagonist of (i) from 1 ng/ml to 12 ng/ml (or to 10 ng/ml) from 6 hours (or from 12 hours, or from 18 hours) after application to 96 hours (or to 120 hours, or to 144 hours) after application, (ii) optionally from 1 ng/ml (or from 2 ng/ml, or from 3 ng/ml) to 12 ng/ml (or to 10 ng/ml) from 18 hours after application to 96 hours after application, (iii) optionally from 2 ng/ml (or from 3 ng/ml) to 12 ng/ml (or to 10 ng/ml) from 24 hours (or from 18 hours) after application to 120 hours after application.

BRIEF DESCRIPTION OF THE DRAWINGS

FIG. 1 is a graph of the in vitro flux of granisetron through human cadaver skin using an embodiment of a device of the present invention.

FIG. 2 is a graph of the in vitro cumulative delivery of granisetron through human cadaver skin using an embodiment of a device of the present invention.

DETAILED DESCRIPTION OF THE INVENTION

Figure 3:
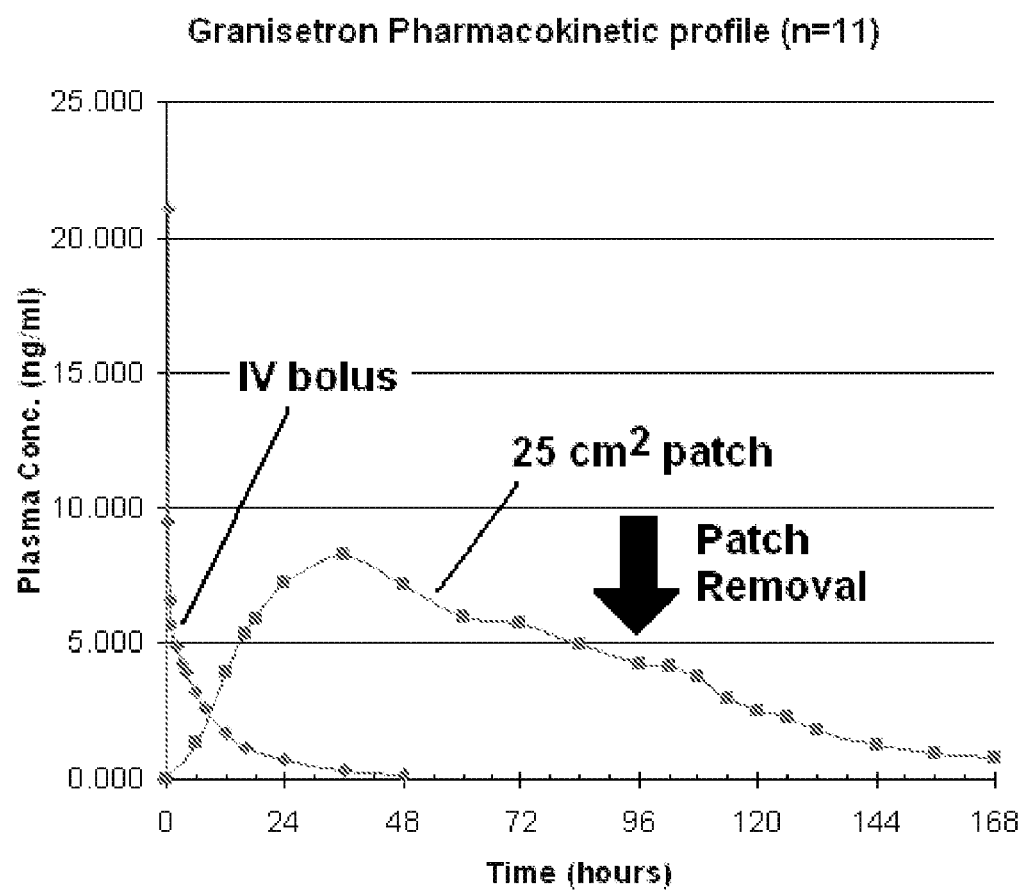
FIG. 3 shows a pharmacokinetic profile obtained using a device of the invention.

As used herein, the term "5-HT$_3$ receptor antagonist" refers to any of a class of drugs which act as 5-hydroxytryptamine receptor antagonists to provide an anti-nausea and anti-vomiting effect in individuals.

As used herein, the term "antiemetic" refers to the prevention, amelioration or treatment of nausea and vomiting in individuals.

As used herein, the term "antiemetic agent" refers to a drug or material that is used to prevent, ameliorate or treat nausea and vomiting in individuals.

As used herein, the term "antiemetically effective amount" refers to the dose or blood level (depending on the context) of an antiemetic agent that provides relief from (including amelioration of) nausea and vomiting in an individual. In the case of blood levels, the level that, if appropriately sustained, provides relief from (including amelioration of) nausea and vomiting in an individual. The amount is an amount that can be expected to be effective in segment(s) of a targeted patient/subject population, and can be such an amount divided by a reasonable number of delivery devices or vehicles.

Blood concentration recitations and other blood-measured pharmacokinetic parameters are, for the purposes of the claims, based on studies of averages across adult (18-65), western, 1$^{st}$ world populations. Cancer patients, for example, may be expected to show higher blood concentrations, perhaps as much as 1.5 to 3 times higher concentrations. Results may vary with sub population (such as of different races), metabolic disposition, regimen of other medications, or the like.

As used herein, the term "individual" refers to a living mammal and includes, without limitation, humans and other primates, livestock and sports animals such as cattle, pigs and horses, and pets such as cats and dogs.

As used herein, the term "onset time" refers to the time after application of the transdermal device or composition to an individual until an antiemetically effective amount is obtained in the individual's blood.

As used herein, the term "permeation enhancement" refers to an increase in the permeability of skin to a therapeutic agent in the presence of permeation enhancer(s) as compared to permeability of skin to the same therapeutic agent in the absence of a permeation enhancer(s).

As used herein, the term "permeation enhancer" refers to an agent or a mixture of agents which acts to increase the permeability of the skin to therapeutic agents.

As used herein, the term "permeation-enhancing amount" refers to an amount of a permeation enhancer which provides permeation enhancement throughout a substantial portion of the administration period.

As used herein, the phrase "portion of intact skin" refers to a defined area of intact unbroken skin or mucosal tissue. That area will usually be in the range of about 5 cm$^2$ to about 100 cm$^2$.

As used herein the term "salt" refers to, but is not limited to, pharmaceutically acceptable organic or inorganic salts. Typical inorganic salts include hydrogen halides such as hydrochlorides, carbonates, phosphates, sulfates, hydrogen sulfates, hydrobromides, nitrates, and sulfides. Organic salts include, but are not limited to, acid addition salts including salts of monocarboxylic and polycarboxylic acids such as acetic acid, malic acid, maleic acid, propionic acid, succinic acid, fumaric acid, citric acid, benzoic acid, cinnamic acid, tartaric acid, and the like.

As used herein, the phrase "sustained time period" refers to about 24 hours or more and will typically intend a period in the range of about 48 or 72 hours to 168 hours.

As used herein, the term "transdermal" refers to both percutaneous and transmucosal administration, i.e., passage of a drug, such as an antiemetic agent through a body surface or membrane such as intact unbroken skin or intact unbroken mucosal tissue into the systemic circulation.

As used herein, the phrase "transdermal device wear time," or "patch wear time" refers to the interval of time during which a transdermal device is maintained in place on a portion of an individual's skin or mucosa.

As used herein, the term "percutaneously absorbable" refers to the ability of a drug to pass through a body surface or membrane such as intact unbroken skin or mucosal tissue into the circulation system when formulated in a transdermal device of the invention.

As used herein, the term "acute nausea and vomiting" relates to nausea and vomiting in an individual lasting up to 24 hours after the individual receives chemotherapy, radiation, or drug treatment. It may also relate to post-operative nausea and vomiting and to nausea and vomiting resulting from motion sickness.

As used herein, the term "delayed nausea and vomiting" relates to nausea and vomiting in an individual occurring up to five (5) days after the individual receives chemotherapy, radiation, postoperatively or post drug treatment.

As used herein, the term "anticipatory nausea and vomiting" relates to a conditioned response in an individual after the individual receives chemotherapy, radiation, or drug treatment if the individual expects to experience nausea and vomiting as a result of the treatment or if the individual experienced nausea and vomiting as a result of previous treatments. Anticipatory nausea and vomiting may also be experienced post-operatively or as a result of motion sickness.

As used herein, the term "skin-contacting layer" is a layer of a transdermal device for contacting skin or mucosa.

As used herein, "flux rate" means the rate as modeled from applications of the device to human cadaver skin.

The present invention relates to methods of preventing, ameliorating or treating nausea and vomiting for a sustained time period by the transdermal administration of antiemetic agents. The antiemetic agents used in the present invention are, in the transdermal device, the free base form of 5-HT$_3$ receptor antagonists, examples of which include ondansetron, granisetron, tropisetron, dolasetron, hydrodolasetron, azasetron, ramosetron, lerisetron, indisetron, itasetron, palonosetron, lamosetron, allosetron and mixtures thereof. It will be recognized that after administration the antagonists will form similar salts or metabolites as are formed given other means of administration or the administration of salt forms. The present invention also relates to devices and compositions for use with the method of the invention.

The method of the present invention is effective in the prevention, amelioration or treatment of nausea and vomiting due to chemotherapy, radiation therapy, other drug therapy, motion sickness, hyperemesis gravidarum, or post-operative reaction. Because this method involves the transdermal administration of an antiemetic agent over the course of days, it is effective in preventing, ameliorating or treating nausea and vomiting for an extended time. Additional benefits of the present invention include improved patient compliance, since the method involves the placement of a transdermal device, which in some embodiments is left in place for 2, 3, 4, 5, 6, 7 days or more; patient protection from nausea and vomiting from the time the device is applied until it is removed, or for extended periods, such as 6, 9, 12, 18 or 24 hours or more, after it is removed; increased patient confidence to leave the hospital or doctor's office after chemotherapy, knowing that the device will prevent or reduce nausea and vomiting. Additionally, the device can maintain blood levels of the antiemetic agent in a therapeutically effective range until it is removed. In some embodiments, after wearing the device for 24 hours or more (or 36 hours or more, or 48 hours or more, or 72 hours or more, or 96 hours or more, or 120 hours or more), blood levels are maintained in therapeutically effective range for an extended period after removal, such as 6, 9, 12, 18 or 24 hours or more. Since the device delivers the antiemetic agent at a controlled rate, there is no initial spike in plasma concentration as when the agent is administered, for example, by IV; therefore, the method reduces side effects, such as headache and constipation, sometimes experienced with other forms of administration.

In certain embodiments, therapeutically effective blood levels of 5-HT$_3$ receptor antagonist are obtained within 24 hours of application, 18 hours of application, 12 hours of application, or within 9 hours, or within 8 hours, or within 7 hours, or within 6 hours. Such onset periods will vary with the 5-HT$_3$ receptor antagonist and the particular skin-contacting layer formulation.

In certain embodiments, the patch provides a flux rate of 1 $\mu g/cm^2/hr$ or more (such as between 1 and 25 $\mu g/cm^2/hr$) of the 5-HT$_3$ receptor antagonist for, after an onset period, 24 hours or more, 48 hours or more, or 72 hours or more, or 96 hours or more, or 120 hours or more, or 144 hours or more, or 168 hours or more. In certain embodiments, the patch provides a flux rate of 2 $\mu g/cm^2/hr$ or more (such as between 2 and 10 $\mu g/cm^2/hr$) of the 5-HT$_3$ receptor antagonist for, after an onset period, 24 hours or more, 48 hours or more, or 72 hours or more, or 96 hours or more, or 120 hours or more, or 144 hours or more, or 168 hours or more.

In certain embodiments, the patch delivers between 10 $\mu g/day$ (microgram/day) or more (such as 10 to 10,000 $\mu g/day$) of the 5-HT3 receptor antagonist to the individual for, from an onset time to 24 hours or more, 48 hours or more, or 72 hours or more, or 96 hours or more, or 120 hours or more, or 144 hours or more, or 168 hours or more. In certain embodiments, the patch delivers between 20 $\mu g/day$ (microgram/day) or more, or 50 $\mu g/day$ or more, 100 $\mu g/day$ or more, 200 $\mu g/day$ or more, 500 $\mu g/day$ or more, 1,000 $\mu g/day$ or more, 2,000 µg/day or more, 4,000 µg/day or more, 6,000 µg/day or more, of the 5-HT3 receptor antagonist to the individual for, from an onset time to 24 hours or more, 48 hours or more, or 72 hours or more, or 96 hours or more, or 120 hours or more, or 144 hours or more, or 168 hours or more. It will be recognized that the amount sought to be delivered will vary with the 5-HT3 receptor antagonist. For example, with ondansentron amounts may need to be higher than for granisetron.

The permeation enhancer used in the device of the present invention can act to increase the permeability of the skin to the $5\text{-HT}_3$ receptor antagonist in the skin-contacting layer. In general, the higher the amount of permeation enhancer, the greater the increase in the skin's permeability; however, at higher amounts of permeation enhancer, cold flow of the adhesive can also occur, making it necessary to remove the transdermal patch prematurely. "Cold flow" is the phenomenon of lateral flow of the reservoir material from under its backing layer or the like. Also at higher amounts of permeation enhancer, the $5\text{-HT}_3$ receptor antagonist may crystallize out of the matrix, thus limiting its permeability. Therefore, it is desirable to use an amount of permeation enhancer which will reliably enhance the drug's permeability while still limiting or preventing adhesive cold flow and drug crystallization. In one embodiment of the device of the present invention, the permeation enhancer in an amount of 15% or less (or about 14% or less, or about 13% or less, or about 12% or less, or about 11% or less, or about 10% or less, or about 9% or less) of the weight of the skin-contacting layer (or composition) to enhance the permeability of the drug without causing significant adhesive cold flow or drug crystallization. The permeation enhancer is present in a permeation-enhancing amount. The permeation enhancer can be present, for example, in an amount of about 0.5% or more (or about 1% or more, or about 2% or more, or about 3% or more, or about 4% or more, or about 5% or more, or about 7% or more) of the weight of the skin-contacting layer (or composition)

The amount of $5\text{-HT}_3$ receptor antagonist can be varied, for example, from about one of the lower limits described below (with the limit exclusive or inclusive of the endpoint), or from to one of the upper limits (exclusive or inclusive). The lower limits are, based on the weight of the skin contacting layer or the composition, 0.1%, 0.2%, 0.5%, 1%, 2%, 3%, or 4%. The upper limits are, based on the weight of the skin contacting layer or the composition, 15%, 14%, 13%, 12%, 11%, 10%, 9%, 8% 7% or 6%. Again, these amounts may additionally vary with the particular 5-HT3 receptor antagonist.

One embodiment of the device of the present invention is a transdermal patch for application to the skin or mucosa of an individual. The patch has a skin or mucosa-contacting layer ("skin-contacting layer" for simplicity) laminated or otherwise attached to a support layer. Typically, the skin-contacting layer is covered by a removable release liner before use to protect the skin-contacting surface and keep it clean until it is applied to the skin or mucosa.

The support layer acts as a support for the skin-contacting layer and provides a barrier layer that prevents loss of the drug in the skin-contacting layer to the environment. The material chosen for such support should be compatible with the adhesive, drug, and permeation enhancer, and should be minimally permeable to any components of the patch. The support can be opaque to protect components of the matrix patch from degradation from exposure to ultraviolet light. Further, the support should be capable of binding to and supporting the adhesive layer, yet should be pliable to accommodate the movements of a person using the patch. Suitable materials for the carrier include metal foils, metalized polyfoils, composite foils or films containing polyester such as polyester terephthalate, polyester or aluminized polyester, polytetrafluoroethylene, polyether block amide copolymers, polyethylene methyl methacrylate block copolymers, polyurethanes, polyvinylidene chloride, nylon, silicone elastomers, rubber-based polyisobutylene, styrene, styrene-butadiene and styrene-isoprene copolymers, polyethylene, and polypropylene. A thickness of about 0.0005 to 0.01 inch can, for example, be used. The release liner can be made of the same materials as the carrier, or other suitable films coated with an appropriate release surface.

Useful adhesives include acrylics (e.g., polyacrylates including alkyl acrylates), polyvinyl acetates, natural and synthetic rubbers, ethylenevinylacetate copolymers, polysiloxanes, polyurethanes, plasticized polyether block amide copolymers, plasticized styrene-butadiene rubber block copolymers, and mixtures thereof. Polyacrylates can be, for example, Duro-Tak 87-4098, Duro-Tak 87-2052, Duro-Tak 387-2353 (or Duro-Tak 87-2353), Duro-Tak 387-2287 (or Duro-Tak 87-2287), Duro-Tak 387-2516 (or Duro-Tak 87-2516) (all from National Starch & Chemical, Bridewater, N.J.), or mixtures thereof. Styrene-butadiene rubber pressure sensitive adhesive can be, for example, DURO-TAK® 87-6173 adhesive (National Starch & Chemical). As is known in the art, adhesive monomers can include carboxylic acid moieties (or salts thereof) and/or other functional groups, such as hydroxyl). Or, adhesive monomers may have no functional monomers (as synthesized, assuming no substantial hydrolysis of, for example, ester linkages). Adhesive polymers are often crosslinked to some degree, such as by use of crosslinking monomer.

If present, the permeation enhancer is typically a fatty acid ester of fatty acyl chain length $C_{12}$-$C_{18}$. The alcohol component of the ester is typically C1-C6, or C2-C4, such as for example isopropanol.

The patch can further comprise various additives in addition to the adhesive, antiemetic, and permeation enhancer. These additives are generally those pharmaceutically acceptable ingredients that are known in the art of drug delivery and, more particularly, in the art of transdermal drug delivery. Nonlimiting examples of additive ingredients include diluents, excipients, emollients, plasticizers, skin irritation reducing agents (which can also include agents that reduce irritation to mucosa), carriers, and mixtures of these. For example, suitable diluents can include mineral oil, low molecular weight polymers, plasticizers, and the like. Many transdermal drug delivery formulations have a tendency to cause irritation after prolonged exposure to the skin or mucosa, thus addition of an irritation reducing agent aids in achieving a composition that is better tolerated by the skin or mucosa.

However, certain embodiments of the current transdermal composition are non-irritating even in the absence of irritation reducing agent. In certain embodiments, the mean cumulative irritation score (measured as in Example 4) is less than 2, or less than 1.5, or less than 1.2, or less than 1.1, or less than 1.0.

For delivery of the antiemetic agent according to an embodiment of the present invention, a patch device containing an adhesive, a 5-HT3 receptor antagonist, and a permeation enhancer is brought in contact with the skin or mucosa at a selected portion of intact skin or mucosa and is held in place by the adhesive.

In certain embodiments, the transdermal composition (prior to application to a patient) is essentially free of water. In certain embodiments, the transdermal composition is essentially free of tetraglycol (also known as glycofurol or tetrahydrofurfurylpolyethilenglycole). In certain embodiments, the transdermal composition is essentially free of a hydrophilic organic solvent, including essentially free of ethanol, isopropanol, butanol, benzyl alcohol, propylene glycol, glycerin, polyethylene glycol having a molecular weight of 600 or less, diethylene glycol monoethyl ether, triacetin, N-methylpyrrolidone, 2-pyrrolidone, dimethyl sulfoxide, decylmethyl sulfoxide, dioxane, lactone or mixtures thereof. For the purposes of the preceding proviso, "hydrophilic organic solvent" does not include fatty acid esters of fatty acyl chain length C12-C18. It will be understood that nominal amounts of such components, when the transdermal composition is essentially free thereof, may be present in amounts consistent with process parameters, but are not present in amounts having a material effect on function, handling, storage, or some factor material to the effective use or marketing of a transdermal device.

In another embodiment the present invention provides a method for the prevention, amelioration or treatment of nausea and vomiting due to chemotherapy, radiation therapy, other drug therapy, motion sickness, or post-operative reaction by the transdermal administration of a 5-$HT_3$ receptor antagonist combined with the administration (e.g., oral, injection (such as IV, IP, IM, SC), transdermal, buccal, rectal) of another antiemetic agent (e.g., a corticosteroid), or the same or different 5-$HT_3$ receptor antagonist administered by separate administration route. A second administration form can be administered by a separate dosing schedule, as appropriate for the given dosage form.

Concurrent administration of 5-$HT_3$ receptor antagonists and corticosteroids for the treatment of nausea and vomiting is known. For example, U.S. Pat. No. 5,929,059 (Sanger et al.) discloses a method of treatment and/or prophylaxis of nausea and vomiting, which comprises administering to a human or animal subject, granisetron and steroid such as dexamethasone or a pharmaceutically acceptable salt or ester thereof. Sanger et al. further disclose that these two ingredients may be administered orally, rectally, parenterally, or buccally, with oral administration being preferred.

However, as earlier described herein, oral administration of anti-emetic compounds can be challenging and may lead to greater discomfort for the patient. Additionally, oral, parenteral (e.g., IV, IM), rectal, and buccal administration of active ingredients produce fluctuation in plasma levels of the active ingredients. Therefore, it would be advantageous to transdermally administer a 5-$HT_3$ receptor antagonist, thus preventing, ameliorating, or treating nausea and vomiting, and then to administer an antiemetically effective amount of an antiemetic corticosteroid, which can enhance the antiemetic properties of the 5-$HT_3$ receptor antagonist. The antiemetic corticosteroid administration can be started at the same time as the beginning of the transdermal administration of the 5-$HT_3$ receptor antagonist or after the 5-$HT_3$ receptor antagonist has been transdermally administered for one hour or more, 12 hours or more, or 24 hours or more. Administrations can be maintained for 12 hours or more, or 24 hours or more, 48 hours or more, 72 hours or more, 96 hours or more, 120 hours or more, 144 hours or more, or 168 hours or more. The corticosteroid administration may occur as a single dosage or additional dosages may be administered at selected intervals. Useful routes of administration include, for example, oral or parenteral routes.

Antiemetic corticosteroids suitable for use in this embodiment of the invention can include, for example, dexamethasone, methylprednisolone, prednisolone, their physiologically acceptable salts or esters, or combinations thereof. Dexamethasone may be administered as dexamethasone alcohol or in the form of a pharmaceutically acceptable salt or ester. Suitable salts and esters include the acetate, isonicotinate, phenylpropionate, pivalate, t-butyl acetate, trioxaundecanoate, disodium metasulphabenzoate and disodium phosphate.

A dose of steroid such as dexamethasone for use according to the method of this embodiment of the invention can, for example, be in the range of 0.5 to 20 mg per dosage unit. The unit doses may be administered from 1 to 4 times per day. However, the exact dose will depend on the route of administration and the condition being treated, and it will be appreciated that it may be necessary to make routine variations to the dosage depending on the age and weight of the patient, as well as the nature and severity of the condition being treated.

Compositions for oral administration of dexamethasone, such as tablets and capsules, may be prepared by conventional means with pharmaceutically acceptable excipients such as binding agents (e.g. pregelatinized maize starch, polyvinylpyrrolidone or hydroxypropyl methylcellulose); fillers (e.g. lactose, microcrystalline cellulose or calcium hydrogen phosphate); lubricant (e.g. magnesium stearate, talc or silica); disintegrants (e.g. potato starch or sodium starch glycollate); or wetting agent (e.g. sodium lauryl sulphate). Tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavoring, coloring and sweetening agents as appropriate.

Preparations for oral administration of the corticosteroid may be suitably formulated to give controlled release of the active ingredient.

For parenteral administration the compositions may be presented in a form suitable for bolus injection or continuous infusion. Formulations for injection may be presented in unit dosage form e.g. in syringes, ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredients may be in powder form for constitution with a suitable vehicle, e.g. sterile pyrogen-free water, before use.

In certain embodiments of this invention a transdermal patch with a skin-contacting layer comprising:
  i. an antiemetically effective amount of a free base of a 5-$HT_3$ receptor antagonist;
  ii. a permeation-enhancing amount of a permeation enhancer selected from the group consisting of isopropyl myristate, isopropyl palmitate or fatty acid esters of fatty acyl chain length C12-C18; and
  iii. an adhesive selected from the group consisting of acrylics (polyacrylates including alkyl acrylics), polyvinyl acetates, natural and synthetic rubbers, ethylenevinylacetate copolymers, polysiloxanes, polyurethanes, plasticized polyether block amide copolymers, plasticized styrene-butadiene rubber block copolymers, and mixtures thereof;

is applied to the skin or mucosa of an individual in need of anti-emetic treatment or prevention. Subsequently, an antiemetically effective amount of a systemic corticosteroid is orally administered to the individual to enhance the antiemetic effectiveness of the 5-HT3 receptor antagonist.

In a further embodiment, the transdermal device is provided together with a systemic corticosteroid, such as dexamethasone, in the form of a kit.

In another embodiment the present invention provides a method for the prevention, amelioration or (including amelioration of succeeding symptoms following prophylactic administration) or treatment of nausea and vomiting due to chemotherapy, radiation therapy, other drug therapy, motion sickness, or post-operative reaction by the transdermal administration of a 5-HT$_3$ receptor antagonist combined with the oral or administration by injection of antiemetic agent(s). The antiemetic agent can be selected from the group consisting of 5-HT$_3$ receptor antagonists, cannabinoids, NK1 receptor antagonists, dopamine antagonists, corticosteroids, or any other known antiemetic agent. In certain embodiments, the antiemetic agent is administered to the individual at the same time that the transdermal device is applied to the individual's skin. In other embodiments, other antiemetic agent(s) are administered with a timing selected to provide an initial delivery to plasma during the lag phase of the transdermal administration.

In one embodiment the transdermal device is provided with an antiemetic agent in the form of a kit. In a further embodiment, the kit comprises labeling describing administering the antiemetic agent to the individual at about the same time that the transdermal device is applied to the individual's skin. Examples of the second component include a dosage form comprising the same or a separate antiemetic agent as in the first transdermal device. The second dosage form can be, for example, for administration orally, by injection (such as IV, IP, IM, SC), transdermally, buccally, rectally, or the like.

In another embodiment, the transdermal device is applied to the individual's skin up to, for example, 24 hours before the individual is to be subjected to an event that creates a risk of emesis. Such events include administration of a pharmaceutical compound that creates a risk of emesis, such as, for example, chemotherapeutic agents for anticancer therapy, and surgical or other medical procedures that create a risk of emesis. In a further embodiment, the transdermal device is applied to the individual's skin 0.5 or more hours (1 or more hours, or 2 or more hours, or 4 or more hours, or 8 or more hours, or 10 or more hours, or 12 or more hours or 24 or more hours or 36 or more hours) before the individual is to be subjected to an event that creates a risk of emesis.

In other transdermal devices adapted to give long-term delivery of granisetron, such long term delivery is achieved by avoiding permeation enhancers. The current invention provides a device that includes such enhancer, but nonetheless provides long term delivery, while at the same time avoiding irritation and instability that can be associated with enhancers. Moreover, in certain embodiments the current device provides, on a device area-normalized basis, greater transdermal delivery to the plasma as measured by peak plasma levels or AUC (area under the curve) than a device that corresponds in all but the absence of permeation enhancer. In certain embodiments, such delivery is 1.5 times or more, or 1.7 times or more, or 2 times or more, as measured at 24, 48, 72, 96 or 120 hours after application of the device.

Example 1

Preparation of Adhesive Mixture and Transdermal Delivery Device

TABLE 1

| | Composition | |
|---|---|---|
| | Formulation A | Formulation B |
| | Patch Size | |
| | 15.0 cm$^2$ | 15.0 cm$^2$ |
| | Estimated Target Daily Dose | |
| | 1.2 mg | 1.2 mg |
| | Dry % | Dry % |
| Styrene-butadiene rubber pressure sensitive adhesive | 44.04 | — |
| Acrylate-vinylacetate pressure sensitive adhesive | — | 43.8 |
| Isopropyl Myristate | 3.01 | 4.07 |
| Granisetron Base | 3.05 | 3.05 |
| Polyester Release liner | 35.8 | 35.8 |
| Polyester Backing | 13.3 | 13.3 |

Components

Formulation A and Formulation B were prepared using the amounts of each component as shown in Table 1 above.

The styrene-butadiene rubber pressure sensitive adhesive used in the examples herein was DURO-TAK® 87-6173 adhesive, available from National Starch and Chemical in Bridgewater, N.J. The acrylate-vinylacetate pressure sensitive adhesive used in the examples herein was DURO-TAK® 87-2516 adhesive, available from National Starch and Chemical in Bridgewater, N.J. The isopropyl myristate used in the examples herein was of NF grade. The polyester release liner used in the examples herein is available from Loparex, Inc., and the polyester backing used in the examples herein is available from 3M as 2610F.

Procedure

The granisetron base is dissolved in an appropriate solvent such as toluene and mixed with the selected adhesive. The isopropyl myristate is then added to the mixture and the contents are mixed until a homogeneous solution is achieved.

The homogeneous solution is coated onto the siliconized surface of the polyester release liner to the desired thickness. The coated release liner is then passed through a drying oven until the solvents are evaporated. The dry adhesive-coated release liner is removed from the oven and is then laminated with the polyester backing layer. The multi-layer laminate is cut by punching out units of the desired size and geometry for delivery of the desired target daily dose, or it may be wound into rolls for storage or transport to another location. The rolled laminate may then be unwound and cut by punching out units of the desired size and geometry. These punched units are then placed in individual pouches and sealed for later use as patches.

Irritation Data

Formulation A was tested in a rabbit irritation test, a guinea pig sensitization test, a dog toxicokinetic and a human irritation test, and found non-irritating and non-toxic.

Example 2

Test for Flux of Granisetron from the Transdermal Delivery Device

Procedure

Heat-separated human cadaver skin was cut to the desired size and mounted on a Franz diffusion cell. The release liner was peeled away from a patch made according to Formulation B as described in EXAMPLE 1 above. The patch was placed on the skin and the patch and skin were clamped together. Receptor solution was added to the diffusion cell, and the assembly was maintained at 32° C. Aliquots of the receptor solution were taken at periodic time points (24 hours, 48 hours, 72 hours, 96 hours, and 120 hours). The concentration of the granisetron in the receptor solution was measured at each time point, and the flux rate from examples A and B was calculated. The resulting data is illustrated in FIG. 1. Cumulative delivery of granisetron over the indicated time was likewise calculated from the concentration of granisetron in the receptor solution at each time point and is illustrated in FIG. 2.

Example 3

Stability of Granisetron in Illustrative Examples

TABLE 2

|  | Composition | |
|---|---|---|
|  | Formulation C Dry % | Formulation D Dry % |
| Styrene-butadiene rubber pressure sensitive adhesive | 49.88% | — |
| Acrylate-vinylacetate pressure sensitive adhesive | — | 43.77% |
| Isopropyl Myristate | — | 5.09% |
| Granisetron Base* | 1.02% | 2.04% |
| Polyester Release liner | 35.8% | 35.8% |
| Polyester Backing | 13.3% | 13.3% |

Patches were made according to the procedure described in Example 1 above using the formulations shown in Table 2. The patches were then tested for granisetron stability using the method described below.

Samples of the patches are stored at 50° C. for up to 2 months. Stability of the product is assessed by testing periodically for granisetron content and the total amount of impurities using high performance liquid chromatography. The results are shown below in Table 3.

TABLE 3

|  | Granisetron Potency (% w/w) | | Total impurities (% of granisetron) | |
|---|---|---|---|---|
| Time | Formulation C | Formulation D | Formulation C | Formulation D |
| $T_o$ | 99.9 | 99.5 | 0.05 | 0.25 |
| 1 month at 50° C. | 99.8 | 99.2 | 0.12 | 0.41 |
| 2 month at 50° C. | 99.6 | 98.4 | 0.19 | 0.81 |

The data in Table 3 show that the granisetron remains stable for at least 2 months at 50° C. in the composition of the example of the invention with little loss of granisetron potency and low amounts of impurities relative to the formulations at starting time $T_o$.

Example 4

Samples for In Vivo Test

Patches were made according to the method described above using the ingredients and respective amounts shown in Table 4.

| Ingredient/Component | Weight (mg/cm$^2$) | % Composition | Wt in finished product (mg/25 cm$^2$ patch) |
|---|---|---|---|
| Granisetron base | 0.75 | 2.54 | 18.75 |
| Isopropyl myristate | 1.20 | 4.06 | 30.00 |
| Acrylic adhesive | 13.05 | 44.13 | 326.25 |
| Total | 15.00 | 50.73 | 375.00 |
| Polyester backing | 3.91 | 13.22 | 97.75 |
| Release liner | 10.66 | 36.05 | 266.50 |
| Total weight | 29.57 | 100.00 | 739.25 |

The acrylic adhesive used in Example 4 was DURO-TAK® 87-2516, available from National Starch and Chemical in Bridgewater, N.J.

A randomized crossover clinical study was conducted in 11 individuals who received either a transdermal patch or an IV solution of granisetron. Each 25 cm$^2$ patch was formulated to deliver 2 mg/day of granisetron. The 25 cm$^2$ patches of Example 4 were applied to the skin of individuals and left in place for 96 hours, at which time they were removed. This was followed by a 10 day wash-out period, after which the same individuals received granisetron IV in once-daily dosages of 2 mg/day Individuals who received the IV treatment in the first period received a transdermal patch in the cross over treatment. Blood plasma levels of granisetron for all of the individuals in the test were measured periodically during the 96 hour time that the patches were being worn and the IV dosages were being administered, and for an additional 2 days after the patches were removed and the IV administration discontinued.

The results (FIG. 3) indicated that the individuals receiving IV granisetron experienced sharp spikes in blood plasma levels of the granisetron after the bolus IV dose was administered and that the blood plasma levels decreased very quickly. On the other hand, the blood plasma levels of granisetron in the individuals wearing the patches increased steadily and reached a plateau that was maintained until the patches were removed after 96 hours, at which time the blood plasma levels decreased slowly and steadily, while still remaining in the therapeutically effective range for more than 24 hours after the patches were removed. With granisetron, typical plasma levels were observed to be in the range of 0.1-25 ng/ml over the whole wear time and for two additional days following patch removal. Thus, the patch of this example provided a blood plasma level in a therapeutically effective range both for the entire patch wear time and for more than 24 hours after it was removed.

Different pharmacokinetic profiles may be seen with different patient sub-populations, as has been seen in one study in Asia. It is unclear if the result reflects differences in genetic variation, hygiene, eating habits, health, competing drug regimens or other factors.

Example 5

Irritation Tests

Patches made according to the formulation in Table 4 were also tested in a cumulative irritation study in 193 healthy volunteers. An active and placebo patch (same patch, with active replaced with adhesive) was applied on the paraspinal regions of each healthy volunteers. The patches were replaced after 5 days with a new set of patches. A total of four such applications were made. Table below shows the single and cumulative irritation scores for the trial. The patch sites were graded according to a 7 point number scale and a letter grade which signified descriptive elements. Letter scores were converted to number scores and added to number scale for the final assessment. Surprisingly, the mean cumulative irritation scores for the active patch were lower than the placebo despite the presence of the active. (0.66 versus 0.83). In addition, as illustrated by the table below, during the first application which represents a typical use, the active patches had significantly larger number of subjects with lower scores compared to placebo.

| {tc "Report" \f C \l 1}{tc "Detailed and/or summarized report" \f C \l 2} | Application | | | | | | | |
|---|---|---|---|---|---|---|---|---|
| | 1 | | 2 | | 3 | | 4 | |
| Converted Score | N | % | N | % | N | % | N | % |
| A—Granisetron TDS | | | | | | | | |
| 0 | 139 | 72.02 | 115 | 59.59 | 105 | 54.40 | 80 | 41.45 |
| 1 | 31 | 16.06 | 42 | 21.76 | 55 | 28.50 | 53 | 27.46 |
| 2 | 20 | 10.36 | 33 | 17.10 | 29 | 15.03 | 47 | 24.35 |
| 3 | 3 | 1.55 | 3 | 1.55 | 4 | 2.07 | 13 | 6.74 |
| | 193 | 100.00 | 193 | 100.00 | 193 | 100.00 | 193 | 100.00 |
| B—Placebo | | | | | | | | |
| 0 | 80 | 41.45 | 98 | 50.78 | 91 | 47.15 | 74 | 38.34 |
| 1 | 76 | 39.38 | 57 | 29.53 | 61 | 31.61 | 65 | 33.68 |
| 2 | 30 | 15.54 | 29 | 15.03 | 31 | 16.06 | 40 | 20.73 |
| 3 | 7 | 3.63 | 9 | 4.66 | 10 | 5.18 | 14 | 7.25 |
| | 193 | 100.00 | 193 | 100.00 | 193 | 100.00 | 193 | 100.00 |

Publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

While this invention has been described with an emphasis upon certain embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed is:

1. A composition for transdermal administration of an antiemetic comprising:
    a skin-contacting composition comprising a mixture of:
        i. an antiemetically effective amount of a 5-HT$_3$ receptor antagonist that is granisetron;
        ii. a permeation enhancing amount of permeation enhancer comprising at least 4% but less than 10% by weight of fatty acid ester wherein said fatty acid ester is of fatty acyl chain length $C_{12}$-$C_{18}$, and wherein said permeation enhancer is less than 10% by weight of the skin-contacting composition; and
        iii. an adhesive,
    wherein a single application of the composition
        provides a plasma concentration of the 5-HT$_3$ receptor antagonist in a therapeutically effective range period of time from an onset time to 12 hours or more after the composition is removed, wherein the onset time is 6 hours or less after application time; and
        provides 75% or more of the area under the curve achieved by a standard of oral dosing of the same 5-HT$_3$ receptor antagonist (either in single or divided doses) for 3 days and, if the composition is applied for five days, provides a mean cumulative irritation score less than 2; and
        provides a plasma concentration of the 5-HT$_3$ receptor antagonist of from 1 ng/ml to 12 ng/ml from 6 hours after application to 120 hours after application, and from 2 ng/ml to 12 ng/ml from 24 hours after application to 96 hours after application,
        wherein properties provided by a single application would be provided by a single application of the skin-contacting composition to 25 cm$^2$ of skin.

2. A composition for transdermal administration of an antiemetic comprising:
    a skin-contacting composition comprising a mixture of:
        i. an antiemetically effective amount of a 5-HT$_3$ receptor antagonist that is granisetron;
        ii. a permeation enhancing amount of permeation enhancer comprising at least 4% but less than 10% by weight of fatty acid ester wherein said fatty acid ester is of fatty acyl chain length $C_{12}$-$C_{18}$, and wherein said permeation enhancer is less than 10% by weight of the skin-contacting composition; and iii. an adhesive, wherein a single application of the composition provides a plasma concentration of the 5-$HT_3$ receptor antagonist in a therapeutically effective range period of time from an onset time to 12 hours or more after the composition is removed, wherein the onset time is 6 hours or less after application time; and provides 75% or more of the area under the curve achieved by a standard of oral dosing of the same 5-$HT_3$ receptor antagonist (either in single or divided doses) for 3 days and, if the composition is applied for five days, provides a mean cumulative irritation score less than 2; and provides a plasma concentration of the 5-$HT_3$, receptor antagonist of from 1 ng/ml to 12 ng/ml from 6 hours after application to 120 hours after application, and from 2 ng/ml to 12 ng/ml from 24 hours after application to 96 hours after application, wherein properties provided by a single application would be provided by a single application of the skin-contacting composition to 25 $cm^2$ of skin, wherein the composition prior to application to a patient is essentially free of water and is essentially free of hydrophilic organic solvent.

3. A composition for transdermal administration of an antiemetic comprising:

a skin-contacting composition comprising a mixture of:

i. an antiemetically effective amount of a 5-$HT_3$ receptor antagonist that is granisetron;

ii. a permeation enhancing amount of permeation enhancer comprising at least 0.5% but less than 10% by weight of fatty acid ester wherein said fatty acid ester is of fatty acyl chain length $C_{12}$-$C_{18}$, and wherein said permeation enhancer is less than 10% by weight of the skin-contacting composition; and iii. an adhesive, wherein a single application of the skin-contacting composition; and iii. an adhesive, wherein a single application of the skin-contacting composition provides a plasma concentration of the 5-$HT_3$ receptor antagonist in a therapeutically effective range period of time from an onset time to 12 hours or more after the composition is removed, wherein the onset time is 6 hours or less after application time; and provides 75% or more of the area under the curve achieved by a standard of oral dosing of the same 5-$HT_3$ receptor antagonist (either in single or divided doses) for 3 days and, if the composition is applied for five days, provides a mean cumulative irritation score less than 2; and provides a plasma concentration of the 5-$HT_3$, receptor antagonist of from 1 ng/ml to 12 ng/ml from 6 hours after application to 120 hours after application, and from 2 ng/ml to 12 ng/ml from 24 hours after application to 96 hours after application, wherein properties provided by a single application would be provided by a single application of the skin-contacting composition to 25 $cm^2$ of skin.

4. The composition of claim 3, further comprising a support layer.

5. The composition of claim 3, wherein, when applied to a portion of intact skin on an individual for 48 hours and then removed, the composition provides the individual with a plasma concentration of the 5-$HT_3$ receptor antagonist in a therapeutically effective range for period of time from an onset time to 12 hours or more after the composition is removed.

6. The composition of claim 3, wherein the 5-$HT_3$ receptor antagonist is in free base form.

7. The composition of claim 3, wherein the permeation enhancer consists essentially of less than 10% of the fatty acid ester by weight of the skin contacting layer.

8. The composition of claim 3, wherein the fatty acid ester, which has an alcohol component of the ester, has a C1-C6 said alcohol component.

9. The composition of claim 3, wherein the fatty acid ester comprises at least 4% but less than 10% of the skin-contacting composition.

10. The composition of claim 1, wherein properties provided by a single application would be provided by a single application of the skin-contacting composition containing 15 to 25 mg of granisetron.

11. The composition of claim 3, wherein the composition prior to application to a patient is essentially free of water and is essentially free of hydrophilic organic solvent.

12. The composition of claim 1, wherein a single application of the composition provides 75% or more of the area under the curve achieved by a standard of oral dosing of the same 5-$HT_3$ receptor antagonist (either in single or divided doses) for 4 days.

13. The composition of claim 1, wherein a single application of the composition provides 75% or more of the area under the curve achieved by a standard of oral dosing of the same 5-$HT_3$ receptor antagonist (either in single or divided doses) for 5 days.

14. The composition of claim 2, wherein properties provided by a single application would be provided by a single application of the skin-contacting composition containing 15 to 25 mg of granisetron.

15. The composition of claim 2, wherein a single application of the composition provides 75% or more of the area under the curve achieved by a standard of oral dosing of the same 5-$HT_3$ receptor antagonist (either in single or divided doses) for 4 days.

16. The composition of claim 2, wherein a single application of the composition provides 75% or more of the area under the curve achieved by a standard of oral dosing of the same 5-$HT_3$ receptor antagonist (either in single or divided doses) for 5 days.

17. The composition of claim 1, wherein permeation enhancer is 4% to 9% by weight of the skin-contacting composition.

18. The composition of claim 2, wherein permeation enhancer is 4% to 9% by weight of the skin-contacting composition.

19. The composition of claim 3, wherein the fatty acid ester, which has an alcohol component of the ester, has a C2-C4 said alcohol component.

20. The composition of claim 19, wherein permeation enhancer is 0.5% to 9% by weight of the skin-contacting composition.

21. The composition of claim 19, wherein permeation enhancer is 4% to 9% by weight of the skin-contacting composition.

22. The composition of claim 3, wherein the fatty acid ester is isopropyl myristate or isopropyl palmitate.

23. The composition of claim 22, wherein permeation enhancer is 0.5% to 9% by weight of the skin-contacting composition.

24. The composition of claim 23, wherein permeation enhancer is 4% to 9% by weight of the skin-contacting composition.

25. The composition of claim 3, wherein the fatty acid ester is isopropyl myristate.

26. The composition of claim 25, wherein permeation enhancer is 0.5% to 9% by weight of the skin-contacting composition.

27. The composition of claim 26, wherein permeation enhancer is 4% to 9% by weight of the skin-contacting composition.

* * * * *